(12) United States Patent
Löhn (10) Patent No.: US 9,291,529 B2
(45) Date of Patent: Mar. 22, 2016

(54) SYRINGE FOR USE WITH A METERING DEVICE

(75) Inventor: Jürgen Löhn, Gross Meckelsen (DE)

(73) Assignee: EPPENDORF AG, Hamburg (DE)

( * ) Notice: Subject to any disclaimer, the term of this patent is extended or adjusted under 35 U.S.C. 154(b) by 805 days.

(21) Appl. No.: 13/615,031

(22) Filed: Sep. 13, 2012

(65) Prior Publication Data

US 2013/0239667 A1    Sep. 19, 2013

Related U.S. Application Data

(60) Provisional application No. 61/541,541, filed on Sep. 30, 2011.

(51) Int. Cl.
*B01L 3/02* (2006.01)
*G01N 1/14* (2006.01)
*G01N 35/00* (2006.01)

(52) U.S. Cl.
CPC ............... *G01N 1/14* (2013.01); *B01L 3/0217* (2013.01); *B01L 3/0234* (2013.01); *B01L 2200/143* (2013.01); *B01L 2300/021* (2013.01); *G01N 2035/00811* (2013.01)

(58) Field of Classification Search
CPC ...... B01L 3/021; B01L 3/0217; B01L 3/0275
USPC ...................................... 73/864.01
See application file for complete search history.

(56) References Cited

U.S. PATENT DOCUMENTS

| 5,002,737 | A | 3/1991 | Tervamaki |
| 2011/0088493 | A1 | 4/2011 | Blumentritt et al. |
| 2011/0224644 | A1* | 9/2011 | Haueter et al. ................. 604/500 |

FOREIGN PATENT DOCUMENTS

| DE | 2926691 A1 | 6/1981 |
| DE | 4342178 A1 | 6/1995 |
| DE | 295 22 141 U1 | 2/2000 |
| DE | 19915771 C1 | 1/2001 |
| DE | 10001938 A1 | 8/2001 |
| DE | 102006009816 A1 | 9/2007 |
| DE | 102009016590 A1 | 10/2010 |
| DE | 10 2009 034 897 A1 | 2/2011 |
| EP | 0657216 A2 | 6/1995 |
| EP | 0691158 A2 | 1/1996 |
| EP | 0951306 A2 | 10/1999 |
| WO | 2004-052543 A1 | 6/2004 |

* cited by examiner

*Primary Examiner* — Hezron E Williams
*Assistant Examiner* — Rodney T Frank
(74) *Attorney, Agent, or Firm* — Vidas, Arrett & Steinkraus, P.A.

(57) ABSTRACT

A syringe with a syringe cylinder and a syringe, with a seat for the syringe cylinder and an axially displaceable piston seat for the syringe piston. There is an encoding on the syringe cylinder with encoding elements as protrusions and deepenings (depressions) at seven encoding positions, checking elements in the form of further protrusions and further deepenings at seven checking positions, each being disposed between two encoding positions. The encoding elements and the checking elements have six protrusions in total, and a guiding structure to align the syringe on a further guiding structure with each encoding element and with each checking element to a sensing element, said further guiding structure being disposed in the seat of the metering device and having a certain position with respect to an annular sensing device for sensing the encoding by sensing elements of the metering device that are across the circumference.

12 Claims, 7 Drawing Sheets

SYRINGE FOR USE WITH A METERING DEVICE

CROSS-REFERENCE TO RELATED APPLICATIONS

This application claims priority to provisional application No. 61/541,541 filed on Sep. 30, 2011.

STATEMENT REGARDING FEDERALLY SPONSORED RESEARCH

Not applicable.

BACKGROUND OF THE INVENTION

The present invention relates to a syringe with an encoding for use with a metering device having a sensing device for sensing the encoding, and a syringe system comprising several syringes having different encodings. Further, the present invention relates to a metering device having a sensing device for sensing an encoding for use with a syringe having an encoding. Further, the present invention relates to a metering system comprising a syringe having an encoding, and a metering device having a sensing device for sensing the encoding. Finally, the present invention relates to a method for operating a metering system comprising a syringe with an encoding, and a metering device with a sensing device for sensing the encoding.

Syringes and metering systems comprising metering devices serve for metering liquids, and are used in biological, chemical and medical laboratories in particular. Metering devices configured as a dispenser permit the stepwise delivery of a liquid from a syringe. The metering amount per delivery step can be adjustable. A dispenser with metering amount adjustment is known from the document DE 29 26 691 C2, the entire contents of which is incorporated herein by reference.

Syringes of different sizes are often offered for metering devices. These have mostly different cross section dimensions. When going over to another syringe size, the set metering amount does no more coincide with the real metering amount. Therefore, metering devices have become known where the syringe has an encoding which is read out by a sensing device of the metering device. An analysing device determines the really inserted syringe size and the really set metering amount, which can be indicated by a display device.

A metering system of the mentioned kind is known from the documents EP 0 657 216 B1, the entire contents of which is incorporated herein by reference, and U.S. Pat. No. 5,620,661A, the entire contents of which is incorporated herein by reference. In these repeater pipettes, the repeater pipette has a seat for a fastening portion of a syringe in a pipette casing, and in an accommodation body a piston seat for the syringe piston of the syringe. In addition, there are fastening devices for reversibly fixing fastening portion and syringe piston in their seats, and piston adjustment devices for moving the accommodation body in the pipette casing. The syringe has an information carrier with information about the syringe and/or the condition thereof, and the repeater pipette has a sensing device for the information on the information carrier. The fastening portion and the syringe piston area adapted to be axially moved into their fastening positions in the repeater pipette via axial openings of their seats, wherein the information carrier arrives in a sensing position with respect to the sensing device. The syringe flange has an annular collar with at least one axially directed sensing surface with an axial position as the information carrier, the syringe being insertable into the repeater pipette in different rotational positions. The sensing device is realised in ring shape, with sensors distributed over the circumference. The sensors have elastically resilient naps which project from a front side of the sensing device facing the axial openings. Preferably, there is an analysing device for the information read out by the sensing device, and a display device for the set metering amount. For reproducible alignment of the syringe with its information carrier to the sensing device, there are alignment noses on the fastening portion of the syringe, and guide grooves in the seat for the fastening portion.

In a practical embodiment, the syringe has seven sensing surfaces on the syringe flange, and the annular sensing device of the repeater pipette has seven sensors that are uniformly distributed over the circumference. Further, the syringe is provided with seven alignment noses which are uniformly distributed over the circumference and are guided on axially directed bridges on a lateral limiting wall of the seat of the repeater pipette, in order to align the sensing surfaces with the sensors.

The alignment noses are each chamfered at the topside, in order to guide the bridges into the noses between the alignment noses when these are not accurately aligned with the bridges. Each alignment nose is disposed between two neighbouring sensing surfaces. The syringes are marketed under the product name "Combitips® Plus, and the pipettes under the product name "Multipipette® Plus" by Eppendorf AG.

The repeater pipette system permits a user to adopt the syringe size according to the practical requirements, and to adjust the metering amount without sumptuous conversion calculations. Instead of the syringe size, the information may also contain other specific data of the syringe and/or of the condition thereof, for instance the degree of purity or a filling substance of the syringe, which is automatically taken into account by the repeater pipette.

In the known repeater pipette system, a malfunction of one or several sensors of the sensing device, wrong insertion of the syringe into the repeater pipette or insertion of a not suitable syringe can lead to erroneous detection and display of the metering amount that is set. As a consequence, erroneous metering may occur.

Further metering systems with syringes having an encoding and sensing devices of the metering device for sensing the encoding are known from the documents EP 0 691 158 B1, the entire contents of which is incorporated herein by reference, and EP 0 951 306 B1, the entire contents of which is incorporated herein by reference. According to EP 0 691 158 B1, the encoding is disposed on the piston of the syringe and the pipetting apparatus has a device for automatic identification of the encoding on the piston. According to EP 0 951 306 B1, the syringe has a series of deepenings on the attachment flanges, which are read out by sensor switches of the metering device when the deepenings move along the sensor switches upon rotation of the syringe. Even in these syringes, display errors may occur due to the mentioned reasons.

Starting from this, the present invention is based on the task to provide a syringe for use with a metering device, a syringe system comprising several syringes for use with a metering device, a metering device for the use with a syringe, a metering system comprising a syringe and a metering device, and a method for operating a metering system, which diminish the risk of erroneous metering. Moreover, there must be the possibility to realise the syringes such that they comply with the practical embodiments of the metering device according to EP 0 657 216 B1.

The syringe of the present invention with a syringe cylinder and a syringe piston for use with a metering device for metering liquids in the laboratory, with a seat for the syringe cylinder and an axially displaceable piston seat for the syringe piston comprises:

an encoding on the upper edge of the syringe cylinder with encoding elements in the form of protrusions and deepenings at seven encoding positions uniformly distributed over the circumferential direction in an arrangement that is characteristic for the type of the syringe, checking elements in the form of further protrusions and further deepenings at seven checking positions, each of them being disposed between two encoding positions on the upper edge of the syringe cylinder, wherein the encoding elements and the checking elements have six protrusions in total, and a guiding structure on the circumference of the syringe cylinder, which has a certain position with respect to the encoding elements and the checking elements in order to align the syringe on a further guiding structure with each encoding element and with each checking element to a sensing element, said further guiding structure being disposed in the seat of the metering device and having a certain position with respect to an annular sensing device of the metering device for sensing the encoding by sensing elements that are uniformly distributed across the circumference.

In addition to the encoding with encoding elements in the form of protrusions and deepenings, the syringe of the present invention has checking elements on the upper edge of the syringe cylinder, in the form of further protrusions and further deepenings. The encoding elements are disposed at seven encoding positions that are uniformly distributed in the circumferential direction, and the checking elements are disposed at seven checking positions, each checking position being located between two encoding positions. The protrusions and deepenings stand out differently far away from the syringe cylinder in the axial direction of the syringe, i.e. in the direction of the syringe piston's displacement in the syringe cylinder. The encoding elements and the checking elements have six protrusions in total. In principle, the syringe can be axially inserted into the seats of a metering device for the upper area of the syringe cylinder and of the syringe piston in any arbitrary rotational position. A guiding structure on the circumference of the syringe cylinder has a certain position with respect to the encoding elements and the checking elements. Through this, it is ensured that when inserting the syringe into the seats, the guiding structure is guided by a further guiding structure in the seat of a metering device having a certain position with respect to an annular sensing device of the metering device, such that each encoding element and each checking element is aligned with an individual one of the sensing elements. The sensing elements are sensors which can determine whether a protrusion is directed towards the sensing element. For this purpose, sensors can be used in particular which are actuated by a protrusion and are not actuated by an depression, or sensors which are actuated by a protrusion in a way which is different from that of an depression. The syringe permits to check whether the encoding is sensed without errors. Only when the sensing device senses six protrusions in total, error-free sensing of the encoding is possible. If less or more than six protrusions are sensed, there is an error which might be due, for instance, to incorrect insertion of the syringe into the metering device, a malfunction of the sensing device or the use of a not suited syringe. Erroneous metering can be avoided by detecting an error.

In that the encoding elements and the checking elements have six protrusions in total, sensing the encoding elements and the checking elements is accompanied by only small energy consumption and small load of the sensing elements. Moreover, the force for the insertion of the syringe and the metering device is small because only a few sensing elements must be actuated.

Like the already known syringes Combitips® Plus of Eppendorf AG, the syringe of the present invention has an encoding with encoding elements at seven encoding positions. Thus, it is possible to produce syringes of the present invention with the same encodings as the known syringes Combitips® Plus. But in difference to the known syringes, the additional checking elements of the syringes of the present invention permit error detection in the process of sensing the encoding. For this purpose, the syringes of the present invention are inserted into metering devices having a sensing device, which senses the encoding elements and the checking elements. Syringes of the present invention which have the same encoding and guiding structures associated to the encoding like the Combitips® Plus can also be put into conventional metering devices Multipette® Plus of Eppendorf AG, whose sensing device senses only the encoding elements. Thus, the conventional metering device Multipette® Plus of Eppendorf AG can also sense the encoding of the syringes of the present invention, and display the metering volume that is set. However, error detection due to sensing of encoding elements and checking elements cannot be performed in this possible utilisation.

An additional surprising advantage of the syringe of the present invention is that the checking elements can be used as additional encoding elements. Namely, the checking elements can be disposed on the upper edge of the syringe cylinder at different positions with respect to the encoding elements. This permits additional encoding of the syringe. For instance, different syringe volumes can be encoded like in the known syringes Combitips® Plus. The checking elements may encode additional properties of the syringes. In particular, it is possible to differentiate syringes which have the same filling volume but which are distinct from each other by special properties. For instance, these properties can be the material, the filling condition, the purity condition of the syringes or a medium that is filled into them.

The protrusions and/or deepenings have preferably smooth and/or uninterrupted surfaces. But the present invention incorporates also syringes with protrusions and deepenings which are formed by rough and/or interrupted surfaces, provided that the position of their body-remote ends can be palpitated by a sensing device. For instance, protrusions and/or deepenings are incorporated into the invention which have a number of parallel grooves, whose width is smaller than the diameter of the palpitating head of a sensing device, so that the sensing device cannot intrude into the grooves.

According to an advantageous embodiment of the syringe, the encoding elements have at most five protrusions and the checking elements at least one protrusion. With this embodiment, all the encodings of the conventional Combitips® Plus can be implemented.

According to a further embodiment, the syringe has one of the filling volumes and protrusions indicated below only at the encoding positions 1 to 7 associated to the respective filling volume, which are disposed clockwise in succession in a top view towards the upper edge of the syringe cylinder, wherein a checking position having a further protrusion exists between at least two encoding positions:

0.1 ml filling volume with protrusions at encoding positions 4, 6 and 7, 0.2 ml filling volume with protrusions at encoding positions 3, 6 and 7,
0.5 ml filling volume with protrusions at encoding positions 2, 6 and 7,
1.0 ml filling volume with protrusions at encoding positions 2, 5 and 7,
2.5 ml filling volume with protrusions at encoding positions 2, 4, 5, 6 and 7,
5.0 ml filling volume with protrusions at encoding positions 2, 3, 5, 6 and 7,
10 ml filling volume with protrusions at encoding positions 3, 4, 5, 6 and 7,
25 ml filling volume with a protrusion at encoding position 7,
50 ml filling volume with protrusions at encoding positions 5, 6 and 7.

The above-mentioned variants of the syringe have the encodings of the known syringes Combitips® Plus. In the above encodings, the distribution of the protrusions to the different encoding positions is in each case unambiguously associated to a syringe with a certain filling volume, so that the associated filling volume can be unambiguously assigned by way of the respective distribution of the protrusions to different encoding positions, without having to know the position of a special encoding position (e.g. of encoding position 1). Thus, the syringes can be inserted into the metering device in all the arbitrary orientations which are permitted by the guiding structures.

According to a further embodiment, the syringe has one of the filling volumes and protrusions indicated below only at the checking positions 1 to 7 associated to the respective filling volume, which are disposed clockwise in succession in a top view towards the upper edge of the syringe cylinder:
0.1 ml filling volume with protrusions at checking positions 1, 2 and 4,
0.2 ml filling volume with protrusions at checking positions 1, 3 and 4,
0.5 ml filling volume with protrusions at checking positions 1, 3 and 4,
1.0 ml filling volume with protrusions at checking positions 1, 3 and 5,
2.5 ml filling volume with a protrusion on the checking position 1,
5.0 ml filling volume with a protrusion on the checking position 1,
10 ml filling volume with a protrusion on the checking position 1,
25 ml filling volume with protrusions at checking positions 1, 2, 3, 4 and 5,
50 ml filling volume with protrusions at checking positions 1, 2 and 3.

These variants have the encodings of the known Combitips® Plus and checking elements with protrusions at specific positions, wherein the encoding elements and the checking elements have six protrusions in total. In principle, the checking elements with protrusions can also be disposed at other checking positions, provided the total number of protrusions is not changed. Through this, differentiations of syringes having the same metering volume are possible. Even in these variants, the distribution of the protrusions to different encoding positions and checking positions is in each case unambiguously associated to a syringe with a certain filling volume.

According to a further embodiment, the guiding structure has guiding elements which are disposed at positions on the circumference of the syringe cylinder whose mutual distance corresponds to one seventh or several times one seventh of the perimeter of the syringe cylinder, in order to align the syringe on a further guiding structure of a metering device with the encoding elements to sensing elements for encoding elements, and with the checking elements to sensing elements for checking elements. According to a preferred embodiment, seven guiding elements are disposed on the circumference of the syringe cylinder, wherein the mutual distance of neighbouring guiding elements corresponds in each case to one seventh of the perimeter of the syringe cylinder. By the alignment of the encoding elements to associated sensing elements for encoding elements of the metering device, the analysis of the encoding is facilitated. Moreover, by the alignment of the checking elements to sensing elements for checking elements, the potential of supplementary encodings is enlarged with the aid of the checking elements. Further, it is achieved by this that when syringes of the present invention are put into conventional pipettes Multipette® Plus, the encoding elements are aligned with the sensing elements of the sensing device, so that the set metering volume is displayed.

According to one embodiment, the guiding elements are disposed on the circumference of the syringe cylinder or on the circumference of a fastening portion of the syringe cylinder. According to another embodiment, the guiding elements are aligning noses between which there are gaps. The aligning noses serve for introducing axial ribs in a seat of the metering device for syringes into the gaps between the aligning noses.

According to a further embodiment, the alignment noses are each one disposed in a radial direction with respect to the centre axis of the syringe cylinder next to the checking elements, and the gaps are disposed in the radial direction next to the encoding elements.

According to another embodiment, the guiding structures are configured such that the encoding elements and the checking elements are associated to arbitrary sensing elements when the syringe is put into the metering device. By analysing the actuated sensing elements, the analysing device of the metering device of the present invention can determine the encoding through the encoding elements, and as the case may be a supplementary encoding by the checking elements, provided that each syringe is provided with a characteristic pattern of encoding elements and checking elements.

The syringe is preferably made of a plastic material. The syringe cylinder and the syringe piston can be made of the same or of different plastics. According to a further embodiment, the syringe cylinder is made of polypropylene or polyethylene or cyclic olefinic (CO) polymer, and/or the syringe piston is made of polyethylene or polypropylene. Preferably, the syringe cylinder consists of polypropylene, and the syringe piston of polyethylene.

The syringe system of the present invention permits the user to select certain syringes of the system depending on the intended utilisation, and to use them with the aid of a metering device. The selected syringes are characterised by their encoding. The encodings can be read out by way of a metering device of the present invention, wherein a contingency check is performed with the aid of the checking elements.

The metering device of the present invention for use with a syringe having a syringe piston and a syringe cylinder for metering liquids in the laboratory comprises
a seat for the upper end of the syringe cylinder,
an accommodation body with a piston seat for the upper end of the syringe piston,
holding devices for detachably holding the upper end of the syringe cylinder and the upper end of the syringe piston in their seats,
piston adjustment devices for moving the accommodation body relative to the seat, an annular sensing device, disposed in the seat and having at least 14 sensing elements that are uniformly distributed over the circumference, a guiding structure on the circumference of the seat for aligning a further guiding structure on the circumference of the syringe cylinder of a syringe, for aligning seven encoding elements and checking elements, disposed between the encoding elements, to the sensing elements of the sensing device, said encoding elements being uniformly distributed over the upper edge of the syringe cylinder and having the form of protrusions and deepenings in an arrangement of an encoding of the syringe characterising the type of the syringe, the checking elements being in the form of further protrusions and deepenings, and wherein the encoding elements and the checking elements have six protrusions in total, and an electronic analysing device connected to the sensing elements and being configured such that it states an error-free sensing upon the actuation of exactly six sensing elements, and such that it triggers the metering device into an operating condition only in the case of an error-free sensing, said operating condition depending on the encoding of a syringe determined by analysing the switched sensing elements.

The metering device has a sensing device, as well as a further guiding structure for aligning a syringe on its guiding structure with the encoding elements and checking elements to one sensing element for each one thereof. The metering device has 14 or 21 or 28 or another manifold of 7 sensing elements, wherein it has at least 14 sensing elements. The sensing elements are directed parallel to the displacement direction of the accommodation body for the upper end of the syringe piston. The metering device has an analysing device, which states an error-free sensing when exactly six sensing elements are actuated. Namely, in this case exactly six protrusions of the syringe are palpated, which indicates error-free sensing. The notice of error-free sensing can occur merely within the device, or can be indicated to the user in a display in addition. In case of an error-free sensing, the analysing device triggers the metering device into an operating condition which depends on the detected encoding of the syringe. The operating condition of the metering device comprises for instance the display or another output of the metering volume that is set. Further, the operating condition can comprise the operation of a drive for the piston adjustment devices with a certain power and/or speed or with a certain power profile and/or speed profile. The power and/or speed can be controlled depending on the material and/or the size of the syringe in particular. Further, the operating condition can comprise a certain advancing path of the drive device for the piston adjustment device. For instance, when syringes of different length are used, the advancing path of the piston adjustment device can be adjusted automatically, or at given metering volume, the advancing path which is necessary for this can be adjusted automatically, depending on the inserted syringe.

The metering device of the present invention is used with syringes of the present invention in order to avoid erroneous metering.

According to one embodiment, the analysing device is configured such that it states an erroneous sensing when another number than six sensing elements are actuated, and triggers the metering device into an error condition. The error condition of the metering device can comprise to display and/or to indicate in another way an error message and/or hints for possible error reasons and/or for the elimination thereof and/or the stop of metering.

BRIEF SUMMARY OF THE INVENTION

The present invention comprises metering devices which are realised as handheld metering devices, i.e. which have a casing like a handle which the user can hold in his/her hand in the metering, in order to direct the syringe to the site of liquid pick-up and liquid delivery. The invention further comprises stationary metering devices. The invention further comprises metering devices wherein the piston adjustment device and/or the device for holding the syringe in the metering device and/or for detaching the syringe from the metering device can be driven by muscle force. The invention further comprises metering devices wherein all or a part of the mentioned devices can be driven by a servo drive, i.e. by means of a (preferably electric) drive motor, which supports the use of muscle force. The invention incorporates also metering devices which have an electronic sensing device and an electronic analysing device, and as the case may be electronic display devices (for instance a LCD-display) or another electronic output device.

The sensing device can have mechanical, electric, optical, magnetic, inductive, capacitive or acoustic sensing elements. Combinations of the sensing elements mentioned above are also possible. The sensing elements are preferably microswitches.

The analysing device is preferably an electronic analysing device. But a merely mechanical analysing device or another analysing device can be considered also.

The sensing device and/or the analysing device and/or display device can be implemented in particular as described in EP 0 657 216 B1 and U.S. Pat. No. 5,620,661A. The statements in the mentioned patent publications relating to this are incorporated into the present application by reference.

The metering system of the present invention comprises the advantageous effects which have been indicated above with respect to the syringe and the metering device.

In the method of the present invention for operating a metering system, a syringe according is detachably connected to the metering device, the encoding elements and the checking elements being aligned with the sensing elements of the metering device, the encoding elements and the checking elements are sensed by means of the sensing device, and the analysing device triggers the metering device into an operating condition that depends on the encoding determined by the sensing device only then when it states the actuation of six sensing elements.

In this method it is ensured that an operating condition of the metering device which depends on the detected encoding is reached only then when the check has given the result that the encoding elements and the checking elements are read out without errors. Thus, erroneous metering is avoided.

According to one embodiment, the analysing device states an erroneous sensing and triggers the metering device into an error condition when it detects another number than six sensing elements. The error condition can comprise in particular the display and/or another output of an error notification and/or hints to possible error reasons and/or to the removal thereof and/or the stopping of the metering.

The present invention will be explained in more detail by the attached drawings of examples of its realisation.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated In the following explanation, the indications "up" and "down" relate to the preferred orientation of the syringe and the metering device in the operation, wherein the syringe and the metering device are each oriented vertically, the syringe having its encoding elements and checking elements at the upper end, and the metering device having its seat with the sensing device at the lower end. In this orientation, the syringe is disposed at the downside with its pick-up- and delivery opening, in particular when the syringe is put into the metering device.

Figure 1A:
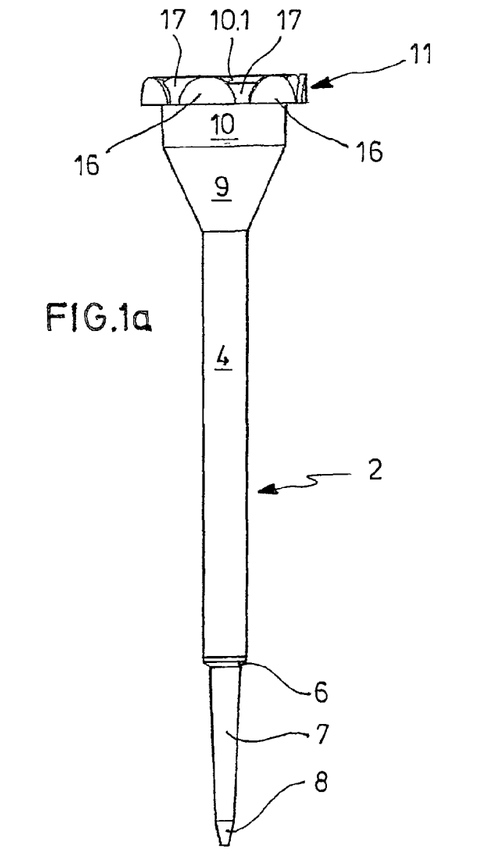
FIG. 1a-d a syringe cylinder of a syringe with a filling volume of 1.0 ml in a side view (FIG. 1a), top view (FIG. 1b), view from the downside (FIG. 1c) and in a magnified partial perspective view obliquely from the top and from the side (FIG. 1d)
Figure 1B:
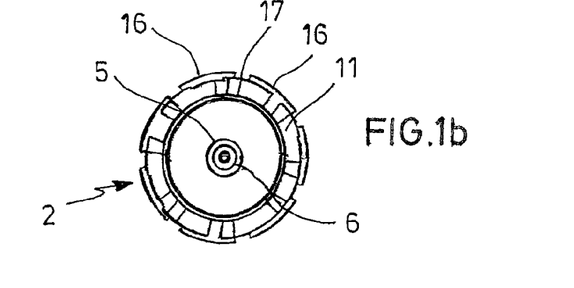
Figure 1C:
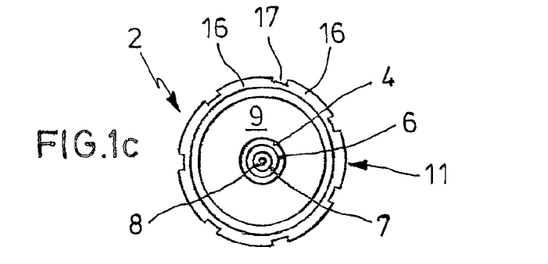
Figure 1D:
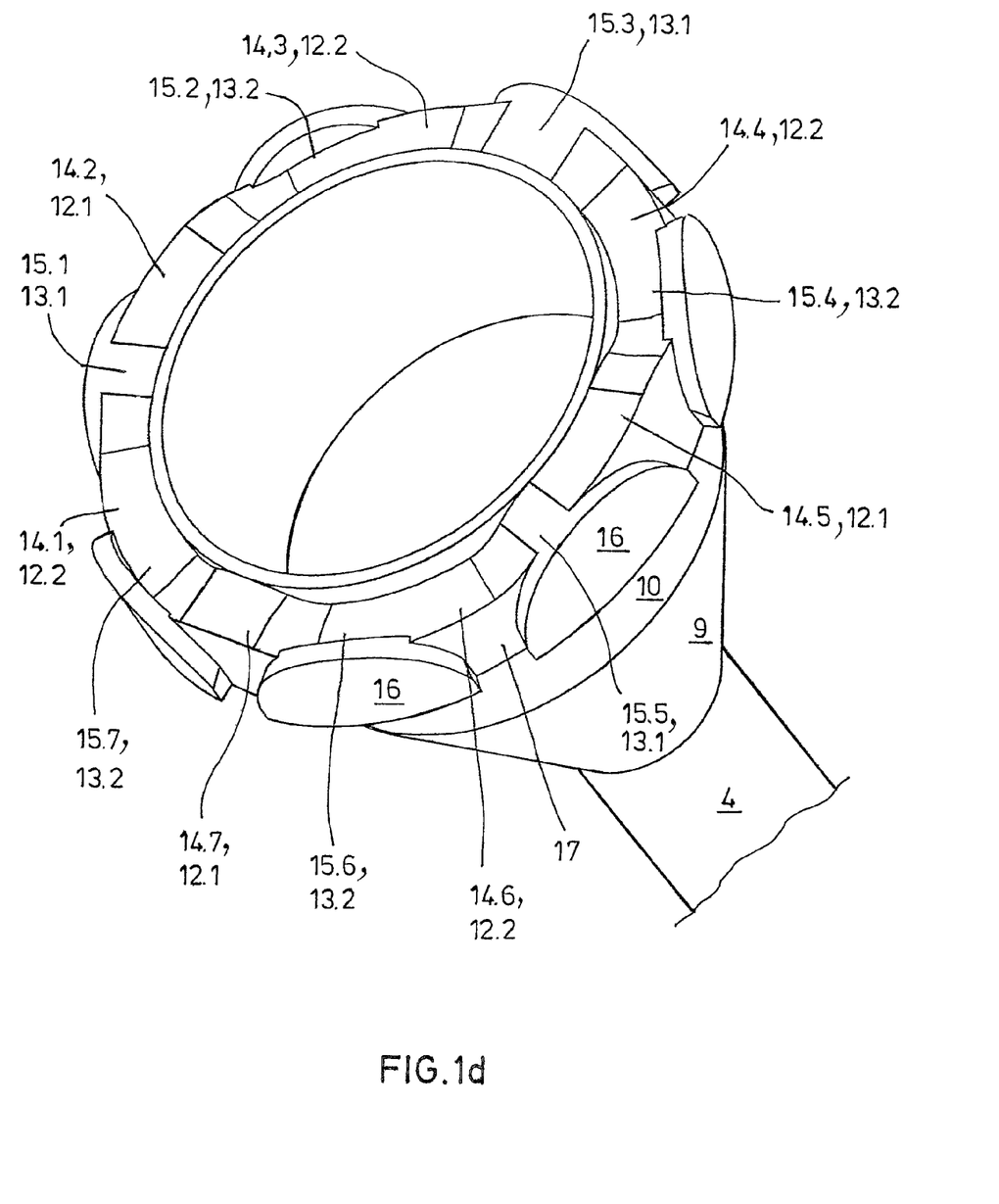
Figure 2:
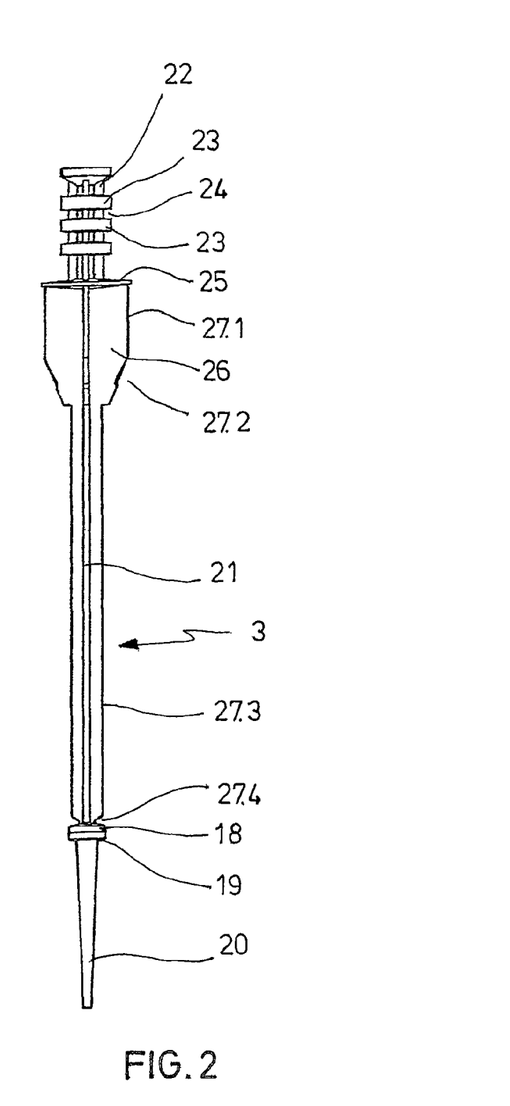
FIG. 2 a syringe piston of the same syringe in a side view.
Figure 3A:
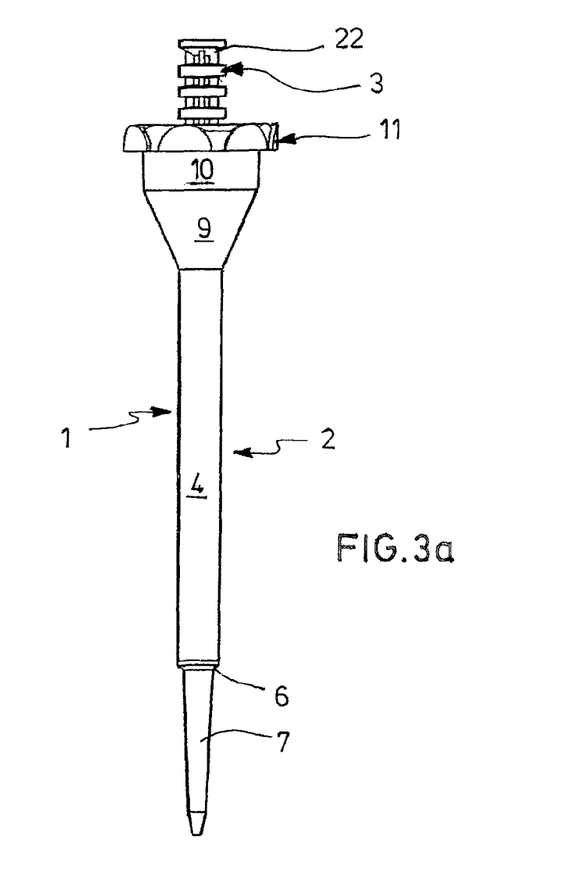
FIG. 3a-c the same syringe assembled in a side view (FIG. 3a), top view (FIG. 3b) and bottom view (FIG. 3c)
Figure 3B:
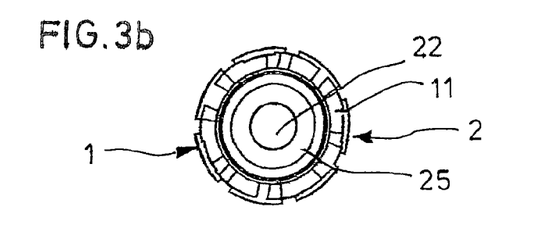
Figure 3C:
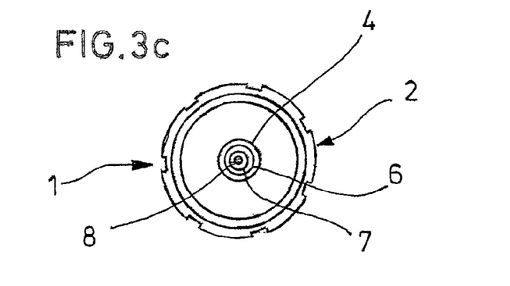

In FIGS. 1 to 3, a syringe 1 with a filling volume of 1.0 ml is shown. It has a syringe cylinder 2 and a syringe piston 3. The syringe cylinder 2 is not strictly cylindrical everywhere in the geometrical sense. It has a cylinder portion 4 which is cylindrical at the inside and the outside and has a cylindrical piston path 5 at the inside.

Via a shoulder 6, the lower end of the cylinder portion 4 is connected to a tip portion 7 which is conical at the inside and the outside and to which joins a more conical cone portion 8 at the downside.

In syringes of the present invention with greater volumes, the shoulder 6 can be designed as a bottom with a central hole to which the conical tip portion 7 joins. In syringes with smaller volume, the shoulder 6 can be omitted completely, and the conical tip portion 7 may directly join the cylinder portion 4.

The upper end of the cylinder portion 4 is connected to a transition area 9, which is conical at the inside and the outside and which broadens upwardly. The upper end of the transition area 9 is connected to an upper cylinder portion 10 which is cylindrical at the inside and the outside and which can serve as a centering area, like described in EP 2 279 791 A1. In syringes of the present invention with greater volume, the transition area can be omitted and the cylinder portion can merge directly into the upper cylinder portion 10.

The upper cylinder portion 10 is in turn connected to a fastening portion 11 in the form of a toroidal flange which forms the upper edge of the syringe cylinder 2.

On the topside of the fastening portion 11, there are encoding elements 12 and checking elements 13 in the form of axially projecting protrusions 12.1, 13.1 and axially standing back deepenings 12.2, 13.2. The encoding elements 12 are located at seven encoding positions 14.1 to 14.7 which are uniformly distributed in the circumferential direction. One checking element 13 is always disposed between two encoding elements 12. The checking elements are located at seven checking positions 15.1 to 15.7 which are uniformly distributed in the circumferential direction. Thus, seven encoding elements 12 in total and seven checking elements 13 in total are disposed on the upper edge of the syringe cylinder in an interlaced arrangement.

The number and arrangement of the protrusions 12.1 and deepenings 12.2 of the encoding elements 12 encodes for a syringe 1 having a certain volume. This will be explained in more detail below, by way of FIG. 4.

There are seven alignment noses 16 on the circumference of the fastening portion 11. The alignment noses 16 are uniformly distributed over the circumference. They are formed by projections on the circumference. The two side surfaces of each alignment nose 16 converge upwardly. In the example, they converge in arcuate shape. There is a gap 17 between neighbouring alignment noses 16. Each gap 17 is disposed exactly below an encoding element 12. There are seven gaps 17 in total. The alignment noses 16 are guiding elements of guiding structures.

In the example, the transitions between the neighbouring protrusions 12.1, 13.1 and deepenings 12.2, 13.2 are rounded. In FIGS. 1 b and d, lines are drawn at the topside of the fastening portion 11 on those positions where different curvature radii, or curvature radii and planes meet each other.

On the inner circumference of the flange, the upper cylinder portion 10 has a sleeve-shaped extension 10.1 which slightly projects at least with respect to the deepenings 12.2, 13.2 and which exists for reasons of fabrication. At greater syringe volumes, this extension 10.1 contributes to avoid damages of sealing lips when a syringe piston 3 is introduced into the syringe cylinder 2.

The syringe cylinder 2 is made of plastics in one piece. It is preferably made by injection moulding a thermoplastic material. The thermoplastic material is for instance polypropylene, polyethylene or a cyclic olefinic (CO) polymer, polypropylene being preferred due to its surface properties and optical properties.

The syringe piston 3 has a flat, cylindrical or respectively circular-disc shaped piston portion 18, which has a circulating sealing lip 19 on its circumference. At the downside, the piston portion 18 is connected to a piston tip portion 20, which is designed conically with the same or a similarly small cone angle like the tip portion 7.

At the topside, the syringe piston 3 has a piston rod 21. The piston rod 21 has a coupling piece 22 at the topside. The coupling piece 22 has several radially projecting, circulating piston collars 23, between which exist circulating grooves 24.

Below the coupling piece 22, a disc 25 is disposed on the piston rod 21, which is designed in a circular disc shape.

Four radially projecting wings 26 rest on the piston rod 21 below the disc 25, which are uniformly distributed over the circumference of the piston rod 21. At the topside, the wings are connected to the disc 25, and at the downside to the piston portion 18. Adjacent to the disc 25, the wings 26 have outer edges 27.1, which are parallel to the piston rod 21. There, the wings 26 have maximum width. A first chamfer 27.2 follows up, within which the width of the wings 26 decreases. An outer edge 27.3 follows up again, which is parallel to the piston rod 21. At the downside, the wings 26 have a further chamfer 27.4, within which the width of the wings 26 decreases further.

In syringes with a greater filling volume (from on 2.5 ml), the wings 26 have a constant width, starting from the disc 25 at least up to shortly before the piston portion 18.

The syringe piston 3 is preferably made in one piece of plastic. Further preferred, it is injection moulded from a thermoplastic material. For instance, it is made of polyethylene or polypropylene, polyethylene being preferred because the materials pair of polyethylene for the syringe piston 3 and polypropylene for the syringe cylinder 2 has a small friction. Polypropylene is preferred for the syringe cylinder due to its surface properties and optical properties.

The cylindrical portions and regions of the syringe cylinder 2 and the syringe piston 3 are circularly cylindrical.

When the piston 3 is completely thrust into the syringe cylinder 2, the piston 3 rests on the lower edge of the transition area 9 with the lower edge of the chamfer 27.2. In syringes with a greater filling volume (for example 2.5 ml), the piston portion 18 rests on the shoulder 6 at the inside. At completely thrust-in piston 3, a small ring gap remains between the piston tip portion 20 and the syringe portion 7. At the downside, the disc 25 submerges into the centering area 10. A small ring gap remains between the wings 26 and the piston path area 5, so that the outer edges 27.3 prevent the syringe piston 3 from tilting within the syringe cylinder 2. A somewhat greater ring gap exists between the disc 25 and the adjacent outer edges 27.1 and the centering area 10, which permits the engagement of a centering sleeve according to EP 2 279 791 A1. The coupling piece 22 is partly disposed in the centering area 10, and it partly projects upward over the fastening portion 11.

The statements above apply in principle also to syringes with another filling volume.

Figure 4:
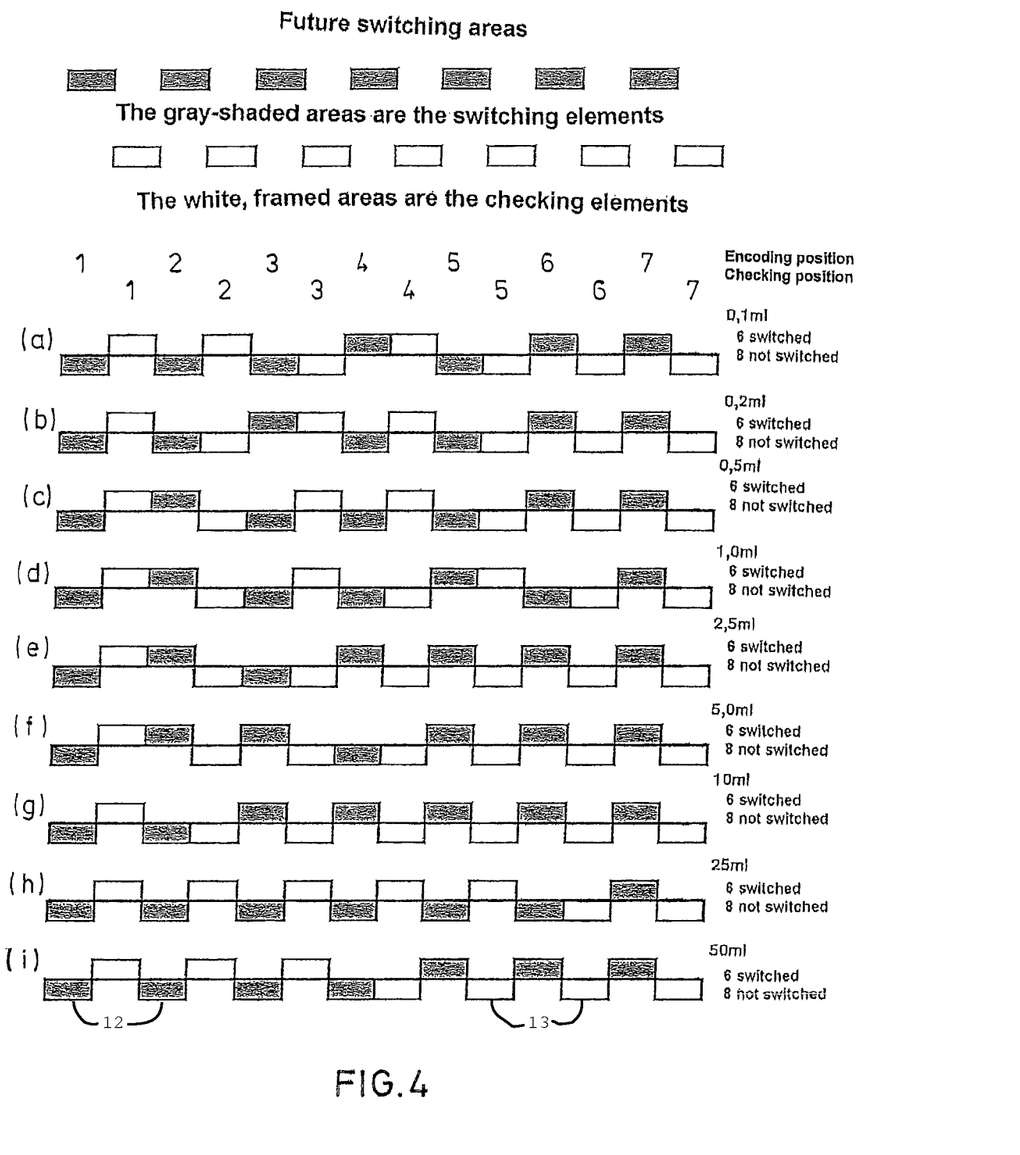
FIG. 4a-i the arrangement of the protrusions and deepenings of the encoding elements and the checking elements of the syringe with a filling volume of 0.1 ml (FIG. 4a), 0.2 ml (FIG. 4b), 0.5 ml (FIG. 4c), 1.0 ml (FIG. 4d), 2.5 ml (FIG. 4e), 5.0 ml (FIG. 4f), 10 ml (FIG. 4g), 25 ml (FIG. 4h), 50 ml (FIG. 4i), always in a developed view.

Examples for encodings of syringes with different filling volumes are indicated in FIG. 4. FIGS. 4a to 4i show the position of the protrusions 12.1, 13.1 and deepenings 12.2, 13.2 on the upper edge of the fastening portion 11 of a syringe cylinder 2, in the flat projection within a plane of a vertical section along a circular line through the upper edge of the syringe cylinder 2.

The grey, framed areas always designate encoding elements 12, and the white, framed areas always designate checking elements 13.

The areas drawn above the respective horizontal line are always protrusions 12.1, 13.1, and the areas drawn below the same horizontal line are always deepenings 12.2, 13.2.

Encoding elements 12 and checking elements 13 of the syringe 1 with a filling volume of 1.0 ml according to FIGS. 1 to 3 are shown in FIG. 4d. Thus, the syringe 1 has protrusions 12.1, 13.1 at the encoding positions 2, 5 and 7 and at the checking positions 1, 3 and 5, and otherwise deepenings 12.2, 13.2. Each syringe has six protrusions and eight deepenings in total.

The encodings of the encoding positions coincide with the encodings of the known Combitips® Plus syringe.

Figure 5:
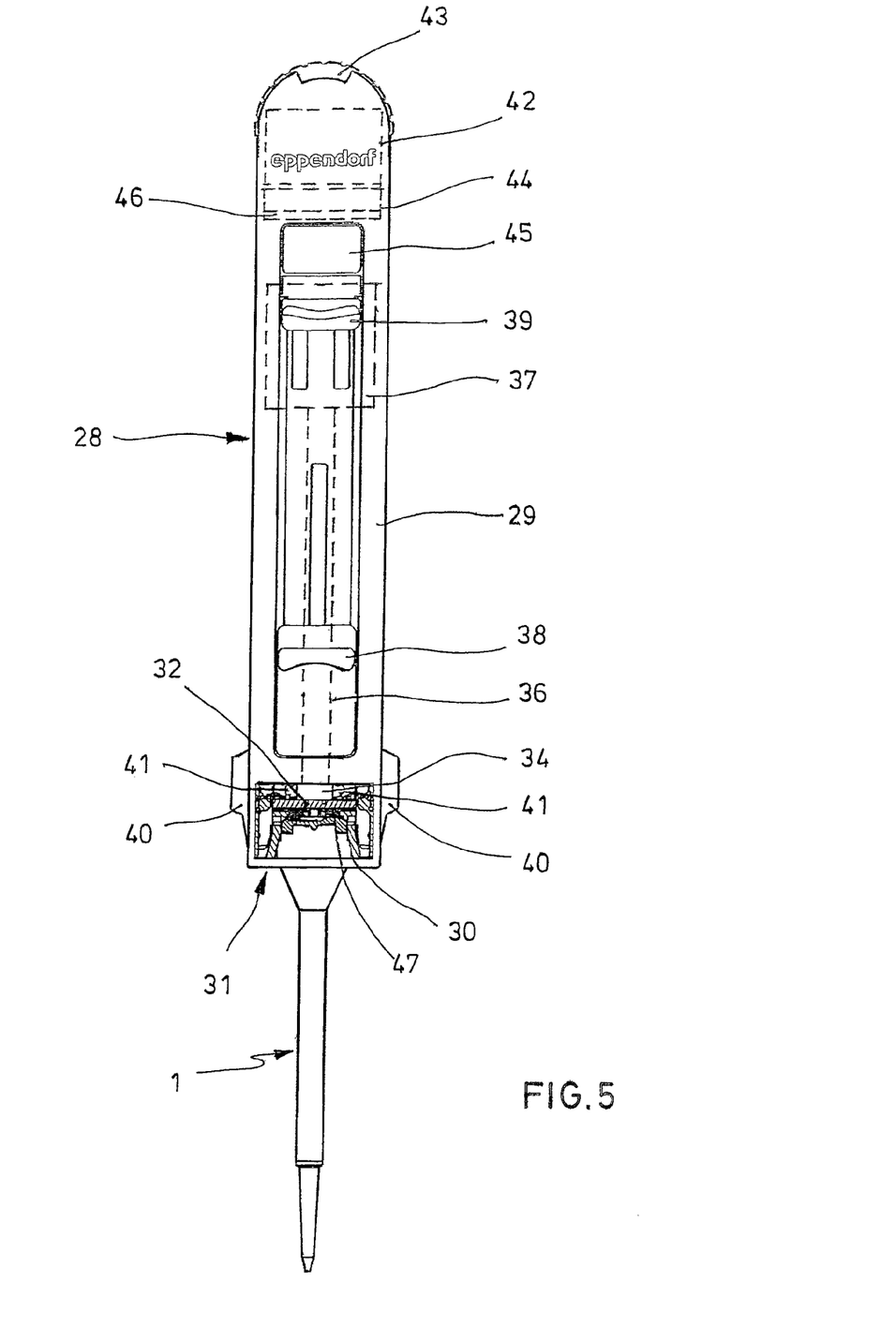
FIG. 5 the syringe of FIGS. 1 to 3, put into a pipette in a partially exploded side view.

According to FIG. 5, a handheld metering device 28 comprises a casing 29, which has a seat 30 at the downside which is accessible from the outside at the lower end through an axial opening 31.

The seat 30 has an approximately circular cross section.

An annular sensing device 32 is disposed on the bottom of the seat 30.

Lateral guiding means in the form of axially running ribs 33 exist on the side walls which laterally limit the seat. In the example, three ribs 33 are distributed over the circumference of the seat 30 (compare FIG. 7).

Above the seat 30, an accommodation body 34 exists in the casing 29 of the metering device 28, with a piston seat 35, accessible form the downside, for the upper end of the syringe piston 3 that is formed by the coupling piece 22. At its upper end, the accommodation body 34 is connected to a drive rod 36 of piston adjustment devices 37 for axial displacement of the accommodation body 34 in the casing 29. The piston adjustment devices 37 have a draw-up lever 38 for drawing up liquid into a syringe 1 that is to be connected to the metering device 28. Further, they have a metering lever 39 for discharging liquid from a syringe 1.

Fastening devices 40, 41 in the form of radially advanceable gripping devices for a syringe cylinder 2 and for a syringe piston 3 are associated to the seat 30 and the accommodation body 34. The fastening devices 40, 41 are designed as pivotally mounted gripping levers, which co-operate when a syringe 1 is being detached from the metering device 28.

On the topside of the casing 29 of the metering device 28, there is an adjustment device 42 for a metering step width, with an adjustment dial 43 and being coupled to the piston adjustment devices 37. Further, on the topside of the casing 29 there is an analysing device 44, which is connected to the sensing device 32 and the adjustment device 42 in order to determine the respective metering- or dispensing volume by means of the encoding of an inserted syringe 1 determined by the sensing device 32, and by means of the metering step width given by means of the adjustment device 42. For this purpose, the adjustment device 42 can have a rotational angle transmitter which detects the rotational position of the dial 43.

The analysing device 44 is connected to a display device 45 in the form of LCD display which is disposed at the topside of the casing 29 and which displays the respective dispensing volume that is set. Further, the casing 29 contains a power supply 46 in the form of a battery or of an accumulator.

An example for a metering device with the features described above is described in EP 0 657 216 A2 and in U.S. Pat. No. 5,620,661A. The statements related to this are incorporated into the present application by reference.

Figure 6:
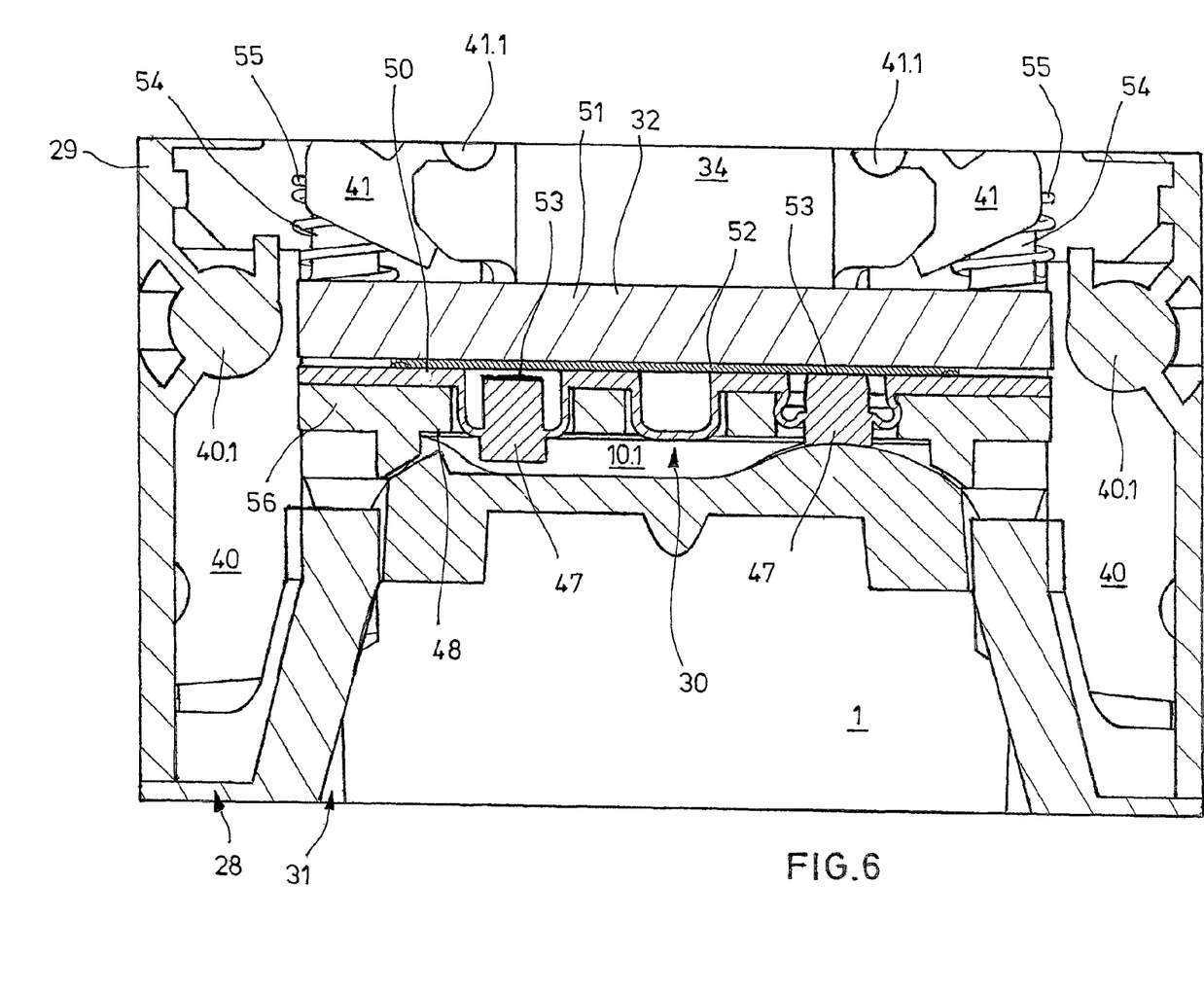
FIG. 6 the exploded part of the metering device of FIG. 5 in an enlarged detail view.
Figure 7:
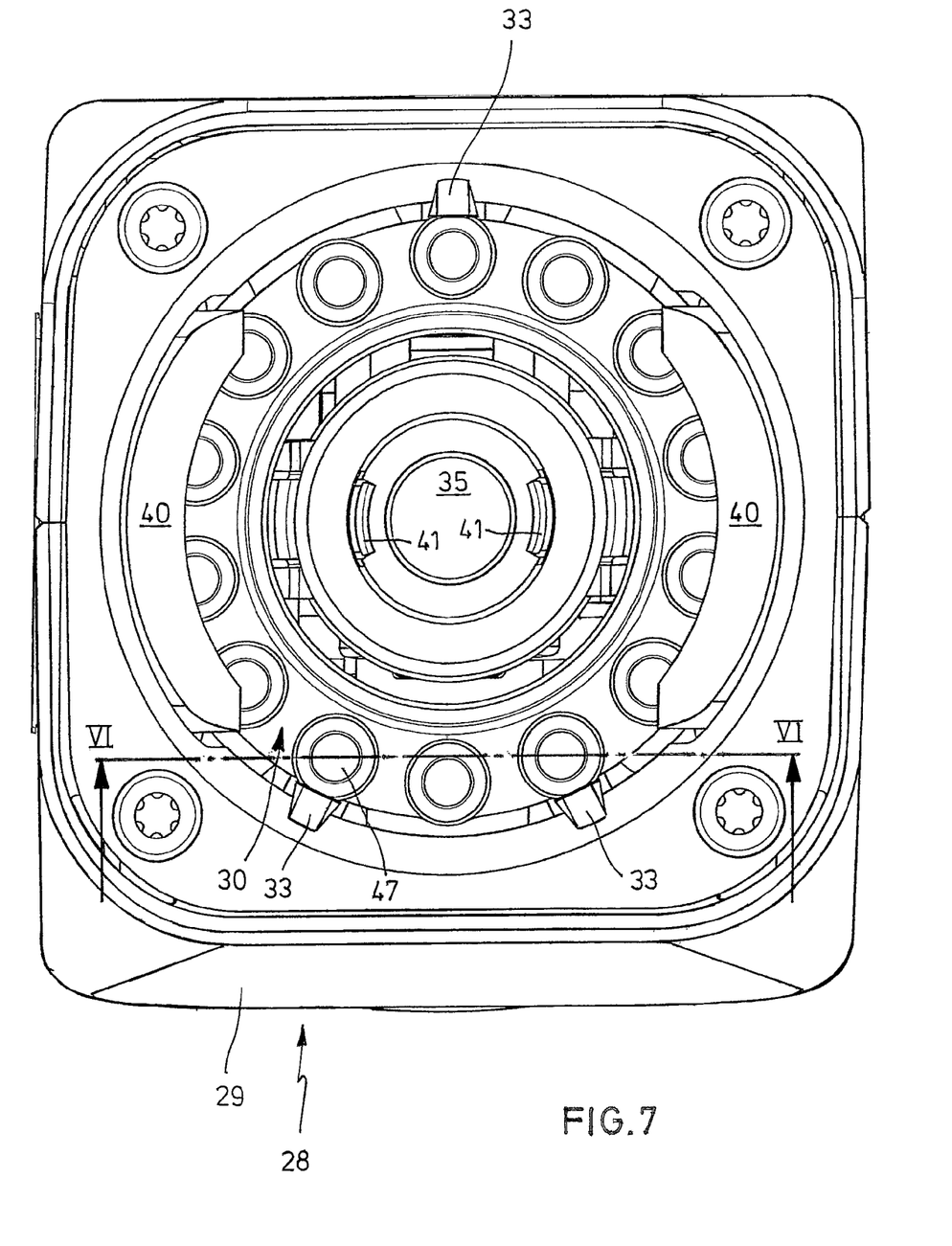
FIG. 7 the metering device of FIG. 5 in an enlarged bottom view.

In FIGS. 6 and 7, details of the annular sensing device 32 are shown. FIG. 6 is a cut along the line VI-VI of FIG. 7. The sensing device 32 has fourteen sensors, distributed uniformly over the circumference. They have sensing elements 47 in the form of palpating buttons projecting from a ring surface 48 of the circularly annular disc shaped sensing device. The sensing elements 47 are designed as naps of an annular disc 50 made of silicone, which rest on an annular circuit board 51 with conductive bands 52 at the side facing the annular disc 50. At the topside, the sensing elements 47 carry an electrically conductive material 53 in the form of a conductor pill or a conductive lacquer. When a sensing element 47 is pushed upward, the conductive material 53 contacts two conductive bands 52 and connects them electrically with each other. A circuit is closed by this (FIG. 6, right side). After unloading, the sensing element jumps resiliently back into its unloaded starting shape (FIG. 6, left side).

At the topside, the circuit board 51 carries projecting stud bolts 54, which are axially guided in holes of a not shown, casing-fixed mounting plate. Helical springs 55 rest on the stud bolts, via which the circuit board 51 is spring-supported on the mounting plate.

An annular guiding means 56 is disposed below the annular sensing device 32, which prevents damage of the annular sensing device 32. Details of the sensing device 32 and the annular guiding means 56 and of their co-operation are described in EP 2 236 207 A1. The relevant statements of this patent publication are incorporated into the present application by reference.

According to FIGS. 5 and 6, a syringe 1 put into the seat 30 through the axial opening 31 is held in the metering device 28 according to FIGS. 1 to 3. The syringe cylinder 2 is detachably held in the seat 30 by the fastening devices 40, and the syringe piston 3 is detachably held in the accommodation body 34 by the fastening devices 41 engaging into the grooves 24. In FIG. 6, the fastening devices 40, 41, designed as pivotally mounted gripping levers, are shown on the axes 40.1, 41.1 of pivot bearings. The guiding structures 16 (compare FIG. 1) and further guiding structures 33 (compare FIG. 7) direct the syringe 1 in the seat 30 in a rotational position in which the encoding elements 12 are aligned with sensing elements 47 for encoding elements, and the checking elements 13 with sensing elements 47 for checking elements. The syringe 1 is axially supported on the annular guiding means 56.

Only those encoding elements 12 and checking elements 13 which have protrusions 12.1, 13.1 actuate sensing elements 47. The analysis of the signals provided by the sensing elements through the analysing device 44 can be triggered in that at least one sensing element 47 is actuated. Only when the analysing device detects that six sensing elements 47 have been actuated, the metering volume that was set is displayed. The encoding acquired by the sensing elements 47 for encoding elements 12 is analysed for this purpose. Further, the setting of the adjustment device 42 for the metering step width is determined. With the aid of these data, the analysing device 44 calculates the delivered metering amount which is displayed by means of the display device 45.

If the analysing device 44 detects that less or more than six sensing elements 47 are actuated, the display device 45 gives a hint of an error, and as the case may be proposals how to eliminate it.

The syringe 1 can be detached from the metering device 28 by actuating the fastening devices 40, 41. Thereafter, another syringe 1 of the same type or of another type can be put in, which is checked anew in the manner described above.

This completes the description of the preferred and alternate embodiments of the invention. Those skilled in the art may recognize other equivalents to the specific embodiment described herein which equivalents are intended to be encompassed by the claims attached hereto.

What is claimed is:

1. A syringe with a syringe cylinder (2) and a syringe piston (3) for use with a metering device (28) for metering liquids in a laboratory, with a seat (30) for the syringe cylinder (2) and an axially displaceable piston seat (35) for the syringe piston (3), comprising
    an encoding on an upper edge of the syringe cylinder (2) with encoding elements (12) in the form of protrusions (12.1) and deepenings (12.2) at seven encoding positions (14.1 to 14.7), uniformly distributed over the circumferential direction on said upper edge of the syringe cylinder in an arrangement that is characteristic for the type of the syringe (1),
    checking elements (13) in the form of further protrusions (13.1) and further deepenings (13.2) at seven checking positions (15.1 to 15.7), each of them being disposed between two encoding positions (14.1 to 14.7) on the upper edge of the syringe cylinder (2),
    wherein the encoding elements (12) and the checking elements (13) have six protrusions (12.1, 13.1) in total, and
    a guiding structure (16) on the circumference of the syringe cylinder (2), which has a certain position with respect to the encoding elements (12) and the checking elements (13) in order to align the syringe (1) on a further guiding structure (33) with each encoding element (12) and with each checking element (13) to a sensing element (47), said further guiding structure (33) being disposed in the seat (30) of the metering device (28) and having a certain position with respect to an annular sensing device (32) for sensing the encoding by sensing elements (47) of the metering device (28) that are uniformly distributed across the circumference.

2. The syringe according to claim 1, wherein the encoding elements (12) have at most five protrusions (12.1) and the checking elements (13) at least one protrusion (13.1).

3. A syringe according to claim 1, which has a filling volume and protrusion (12.1) indicated below only at the encoding positions (14.1 to 14.7) 1 to 7 associated to the respective filling volume, which are disposed clockwise in succession in a top view towards the upper edge of the syringe cylinder (2), wherein a further protrusion (13.1) exists on a checking position (15.1 to 15.7) between at least two encoding positions (14.1 to 14.7):
    0.1 ml filling volume with protrusions at encoding positions 4, 6 and 7,
    0.2 ml filling volume with protrusions at encoding positions 3, 6 and 7,
    0.5 ml filling volume with protrusions at encoding positions 2, 6 and 7,
    1.0 ml filling volume with protrusions at encoding positions 2, 5 and 7,
    2.5 ml filling volume with protrusions at encoding positions 2, 4, 5, 6 and 7,
    5.0 ml filling volume with protrusions at encoding positions 2, 3, 5, 6 and 7,
    10 ml filling volume with protrusions at encoding positions 3, 4, 5, 6 and 7,
    25 ml filling volume with a protrusion on encoding position 7,
    50 ml filling volume with protrusions at encoding positions 5, 6 and 7.

4. The syringe according to claim 3, which has one of the filling volumes and protrusions (13.1) indicated below only at the checking positions (15.1 to 15.7) 1 to 7 associated to the respective filling volume, which are disposed clockwise in succession in a top view towards the upper edge of the syringe cylinder (2):
    0.1 ml filling volume with protrusions at checking positions 1, 2 and 4,
    0.2 ml filling volume with protrusions at checking positions 1, 3 and 4,
    0.5 ml filling volume with protrusions at checking positions 1, 3 and 4,
    1.0 ml filling volume with protrusions at checking positions 1, 3 and 5,
    2.5 ml filling volume with a protrusion on the checking position 1,
    5.0 ml filling volume with a protrusion on the checking position 1,
    10 ml filling volume with a protrusion on the checking position 1,
    25 ml filling volume with protrusions at checking positions 1, 2, 3, 4 and 5,
    50 ml filling volume with protrusions at checking positions 1, 2 and 3.

5. A syringe according to claim 1, wherein the guiding structures (16) are disposed at positions on the circumference of the syringe cylinder (2) whose mutual distance corresponds to one seventh or several times one seventh of the perimeter of the syringe cylinder (3), in order to align the syringe (1) on a further guiding structure (33) of a metering device (28) with the encoding elements (12) to sensing elements (47) for encoding elements, and with the checking elements (13) to sensing elements (47) for checking elements.

6. A syringe according to claim 1, with a syringe cylinder (2) made of polypropylene or polyethylene or cyclic olefinic (CO) polymer, and/or with a syringe piston (3) made of polyethylene or polypropylene.

7. A syringe system comprising at least two syringes (1) with different encodings according to claim 1.

8. A metering device for use with a syringe (1) having a syringe piston (2) and a syringe cylinder (3) for metering liquids in a laboratory, comprising
   a seat (30) for the upper end of the syringe cylinder (2),
   an accommodation body (34) with a piston seat (35) for the upper end of the syringe piston (3),
   holding devices (40, 41) for detachably holding the upper end of the syringe cylinder (2) and the upper end of the syringe piston (3) in their seats (30, 35),
   piston adjustment devices (37) for moving the accommodation body (34) relative to the seat (30),
   an annular sensing device (32), disposed in the seat (30) and having at least 14 sensing elements (47) that are uniformly distributed over the circumference of the seat,
   a guiding structure (33) on the circumference of the seat (30) for aligning a further guiding structure (16) on the circumference of the syringe cylinder (2) of a syringe (1), for aligning seven encoding elements (12) and checking elements (13), disposed between the encoding elements (12), to the sensing elements (47) of the sensing device (32), said encoding elements (12) being uniformly distributed over the upper edge of the syringe cylinder (2) and having the form of protrusions (12.1) and deepenings (12.2) in an arrangement of an encoding of the syringe (1) characterising the type of the syringe (1), the checking elements being in the form of further protrusions (13.1) and deepenings (13.2), and wherein the encoding elements (12) and the checking elements (13) have six protrusions (12.1, 13.1) in total, and
   an electronic analysing device (44) connected to the sensing elements (47) and being configured such that it states an error-free sensing upon the actuation of exactly six sensing elements (47), and such that it triggers the metering device (28) into an operating condition only in the case of an error-free sensing, said operating condition depending on the encoding of a syringe (1) determined by analysing the switched sensing elements (47).

9. The metering device according to claim 8, wherein the electronic analysing device (42) is configured such that it states an erroneous sensing when another number than six sensing elements (47) are actuated, and triggers the metering device (28) into an error condition.

10. The metering device of claim 8 further including at least one syringe.

11. A method for operating a metering system, including the steps of:
    detachably connecting a syringe (1) to a metering device (28), the syringe having encoding elements (12) and checking elements (13) which are aligned to sensing elements (47) of the metering device (28),
    sensing the encoding elements (12) and the checking elements (13) by a sensing device (32) of said syringe,
    said encoding elements (12) and checking elements (13) causing activation with aligned sensing elements (47), and
    triggering the metering device (28) into an operating condition via an analysing device (44) on said metering device that depends on the encoding determined by the sensing device (32) only when it states the actuation of six sensing elements (47).

12. The method according to claim 11, wherein the analysing device (44) triggers the metering device (28) into an error condition when it states another number than six sensing elements (47).

* * * * *